United States Patent [19]

Huch

[11] 4,259,963
[45] Apr. 7, 1981

[54] MULTI-PURPOSE TRANSDUCER FOR TRANSCUTANEOUS BLOOD MEASUREMENTS

[76] Inventor: Albert Huch, Kugelgasse 1, 3550-Marburg, Fed. Rep. of Germany

[21] Appl. No.: 54,600

[22] Filed: Jul. 3, 1979

[51] Int. Cl.³ .............................................. A61B 5/00
[52] U.S. Cl. .................................. 128/635; 128/666; 204/195 B
[58] Field of Search .............................. 128/633–635, 128/637, 665–667; 204/195 R, 195 B, 195 P

[56] References Cited

U.S. PATENT DOCUMENTS

| | | | |
|---|---|---|---|
| 3,930,493 | 1/1976 | Williamson | 204/195 B X |
| 4,185,620 | 1/1980 | Hagihara | 128/635 |

OTHER PUBLICATIONS

Geddes, L. A. et al., "Multi-Function Transducer for Obtaining Digital Volume, Pulse, Skin-Resistance Response and Electrocardiogram", Med. & Biol. Engrg. & Computing, vol. 15, May 1977, pp. 228–232.

Primary Examiner—Kyle L. Howell
Assistant Examiner—Francis J. Jaworski
Attorney, Agent, or Firm—Michael J. Striker

[57] ABSTRACT

A multi-purpose polarographic oxygen-concentration transducer of the transcutaneous-measurement type, a face of it being laid against the tissue of interest, is able to generate signals beyond those indicating mere total oxygen concentration, and can additionally generate signals indicating concentration of oxygen chemically bound to blood hemoglobin, as well as also indicating pulse rate and pulse waveform, blood flow rate through the capillary network of such tissue, the elastic behavior of the capillaries, and the flow rate of blood through such tissue exclusive of that flowing through the capillary network. The transducer is thermostatically temperature-controlled and emits light onto the tissue against which it is laid and detects the light received back by reflection and/or by transmission of such light into and out of the tissue against which the transducer is laid.

12 Claims, 1 Drawing Figure

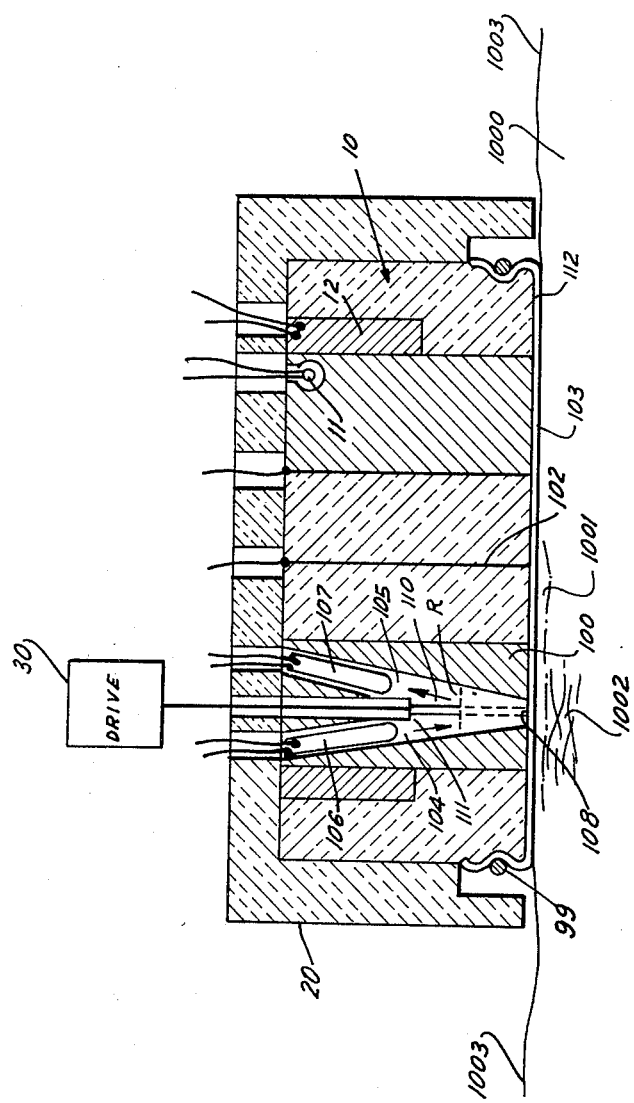

MULTI-PURPOSE TRANSDUCER FOR TRANSCUTANEOUS BLOOD MEASUREMENTS

BACKGROUND OF THE INVENTION

The present invention concerns transducers of the thermostatic type which are used simultaneously to transcutaneously measure the concentration of a gas in the blood in tissue of interest, e.g., the concentration of oxygen, as well as the rate of flow of blood through the tissue of interest. Such a transducer is disclosed, for example, in Federal Republic of Germany published allowed patent application DAS No. 22 55 879.

When such transducers are being used, it is often necessary or desirable to know not merely the oxygen concentration of the blood in the tissue of interest, but also the concentration or amount of oxygen chemically bound to the blood hemoglobin per se.

Likewise, when such transducers are used, it will often be necessary or desirable to know the concentration of blood hemoglobin per se.

Of course, it will very often be necessary to know the pulse rate of the patient, and also the patient's pulse waveform, as well as the rate of blood flow through the capillaries of the tissue of interest and/or the degree of elasticity exhibited by the capillaries as blood is carried through the capillaries.

SUMMARY OF THE INVENTION

It is a general object of the invention to provide a transducer of the type in question, but expanded in its capabilities so as to be able, additionally, to be used for the ascertainment of these further circulatory variables of interest.

In accordance with the present invention, a blood-gas concentration transducer of the type in question is provided with means which emit light from that face of the transducer which is laid against the tissue of interest during the transcutaneous blood-gas concentration measurement, and with photodetector means which receive that light after it has been reflected off and/or transmitted through the tissue of interest.

When the light emitted from this face of the transducer unit passes directly into and through the tissue of interest, especially through skin and accordingly through the capillary network associated therewith, and is then detected by the photodetector means, the thusly transmitted light will exhibit marked alteration in character and/or intensity as a result of such passage through the skin and capillary network.

For example, the light passing through the skin and capillary network on its way from the light source to the photodetector will be variably blocked by the capillaries periodically in correspondence to the patient's pulse, so that the magnitude of the resultant light-signal can serve for indication of pulse waveform, and of course therefore for pulse rate.

When providing the concentration transducer with a light source and photodetector in this manner, this can be extended to furthermore include, for example, five monochromatic light sources and additional photodetector means, to perform a photometric concentration measurement of the type disclosed, for example, in Federal Republic of Germany published patent application DOS No. 23 43 097. Using such multiple-wavelength technique, it is possible to ascertain the ratio of oxygenated to desoxygenated hemoglobin. Then, it becomes possible to ascertain the fraction of blood oxygen which is merely dissolved in the blood. In particular, the oxygen partial pressure is ascertained by means of the polarographic oxygen-concentration transducer of the transducer unit, and this partial pressure indicates the total concentration of oxygen carried in the blood in the tissue of interest. Thus, using the multiple-wavelength technique just referred to ascertain the ratio of oxygenated to desoxygenated hemoglobin, it accordingly becomes possible to ascertain the concentration of oxygen merely dissolved in the blood in the tissue of interest, i.e., at the location at which the transducer unit is laid against the tissue of interest.

As already stated, the magnitude of the light signal generated by the light source and photodetector can be used to ascertain pulse rate and pulse waveform, and therefore also the present vascular elastic behavior or elasticity. Additionally, however, with the oxygen saturation known, the average or mean of the magnitudes assumed by the light signal serves to ascertain hemoglobin concentration as such.

All these various measurements can be performed by means of the thermostatic transducer here in question, which is merely laid against the tissue of interest, additionally in the case of hyperemia, especially when induced by the excess-heat technique. This is of particular significance because then the physiological relationships prevailing in the skin, assuming skin to be the tissue against which the transducer unit is laid, approximately correspond to those prevailing in the body core.

It is furthermore possible, with the multi-purpose transducer of the invention, to ascertain the volumetric flow rate of blood perfused through the tissue of interest. The average or mean value of the light signal produced by the light source and photodetector serves to indicate the elastic behavior of the blood vessels present, as already stated, and thereby vascular flow cross-sectional area. Therefore, if the blood pressure is known, flow rate can be ascertained rather directly from the elementary relationship between flow rate, on the one hand, and, on the other hand, pressure and flow cross-sectional area.

The specific design of the multi-purpose transducer unit of the invention may depend upon the particular applications to be involved. Thus, for example, it is advantageous to employ light-emitting diodes for the light source, because of their low heat generation, when the wavelength spectrum to be used permits this. Any heat generated tends to be more than compensated for by the thermostatic system with which the transducer is anyway provided. If the application involved requires higher-intensity light sources, and/or light sources of more extreme monochromaticity then use can be made of a light source located outside the transducer unit, with a light-conductive fiber structure transmitting the source light to the point of application of the transducer unit to the tissue of interest. It is also possible to provide the transducer structure with light-guiding bores, leading from the light source to the tissue and/or from the tissue to the photodetector. Likewise, light-guiding bores and light-conductive fiber structures can be used in combination for transmitting light from the tissue of interest to one or more photodetectors, and similarly for transmitting to the tissue of interest light from one or more light sources.

When the light emitted from the face of the transducer laid against the tissue of interest is to be transmitted through the tissue of interest, e.g., the skin surface, the skin is not pinched, but instead the transducer is advantageously merely laid flat upon it. Accordingly, to shorten the distance through which the emitted light must actually travel through the skin before emerging from within it, it is advantageous, according to a further feature of the invention, that the direction in which light is emitted into the skin, and the direction in which the photodetector is to receive light emitted from within the skin, both form an angle with respect to the normal to the skin surface. This can be accomplished by corresponding orientation of the light-guiding bores or light-conductive fiber optic structures employed.

In accordance with this latter feature, it is then furthermore of advantage that the light paths terminate at the same surface, i.e., that the beam of light incident on the skin surface from the light source occupy, on the skin surface, the selfsame area as the area from which the photodetector of the transducer unit can pick up light. This makes it possible to alternatively measure by means of reflection, i.e., as an alternative to through-the-skin light measurement. This is a very important further capability for such a multi-purpose transducer, because at certain wavelengths values the pigmentation of the skin, which is variable from one patient to another, does not to any great degree make itself felt in the reflective light measurement performed.

When the two light paths terminate at the same surface area, then it is a further feature of the invention to provide intermediate them a light screen. This assures that the two light paths will not short-circuit a through-the-skin light measurement.

It is a particular advantageous concept of the invention that such light screen be movably mounted between a position isolating the two light paths from each other and a position permitting the two light paths to overlap and coincide at the skin surface. Equivalently, the light screen can be removably mounted, and be simply removed when light-path overlap is to be permitted for a light-reflection measurement. This makes it particularly simple to alternatively, or indeed alternately, perform transmissive and reflective light measurements.

Indeed, it is a related advantageous feature of the invention that the light screen be provided with a drive mechanism which alternately moves it to the two positions just mentioned, so that transmissive and reflective light measurements be performed alternately, automatically.

The novel features which are considered as characteristic for the invention are set forth in particular in the appended claims. The invention itself, however, both as to its construction and its method of operation, together with additional objects and advantages thereof, will be best understood from the following description of specific embodiments when read in connection with the accompanying drawing.

BRIEF DESCRIPTION OF THE DRAWING

The single FIGURE depicts an exemplary embodiment of the present invention.

DESCRIPTION OF PREFERRED EMBODIMENTS

In the FIGURE, numeral 10 denotes in toto a multi-purpose blood-gas concentration transducer embodying the present invention. Numeral 20 denotes the transducer housing. Here, the transducer 10 is a polarographic oxygen-concentration transducer and comprises the usual reference electrode 100, surrounded by and encased in a body of insulating material, and in turn surrounding and encasing a body of insulating material through which passes the measuring electrode 102 of the transducer. Stretched across the lower face of the transducer structure is a permeable membrane 103, e.g., made of Teflon, which is held in place by means of a clamping or tension ring 99 which clamps the marginal portion of membrane 103 into a circumferential groove at the lower end of the outer periphery of the transducer 10.

In the usual way, the membrane 103 confines above it a layer of electrolyte, with which the reference and measuring electrodes are in conductive engagement.

The reference electrode 100 is provided with two light-guiding bores 104 and 105. Bore 104 accommodates a light source 106, such as a light-emitting diode. Alternatively, an exteriorly located light source could be used with a light-conductive fiber structure extending into the bore 104 correspondingly. The light-guiding bore 105 accommodates a photodetector 107; here likewise, a light-conductive fiber structure might instead be used, leading to an exteriorly or otherwise located photodetector.

The light paths defined by the two light-guiding bores 104, 105 overlap at an area 108 at the bottom face 112 of the transducer 10. The bottom face of the transducer 10, across which membrane 103 is placed, is laid against the tissue of interest, here against the surface 1003 of patient's skin 1000. The light emitted by light source 106 is transmitted through membrane 103, but is covered over by the skin 1000.

When a transmissive light measurement is to be performed, a light-blocking screen 110 is lowered from its illustrated position to the position shown in broken lines, i.e., down to the surface 1003 of skin 1000, here through the intermediary of the membrane 103 itself. This isolates the light paths of the light source 106 and photodetector 107, so that the only light from the former actually reaching the latter is that passing through the upper skin 1001 and its capillary network 1002 and, due to internal light transmission, reflection and scattering, emitted back upwards into the light-guiding bore 105, for incidence onto the photodetector 107.

If a reflective light measurement is to be performed, the light-blocking screen 110 is raised up to its illustrated retracted position R, so that the vastly major portion of the light reaching the photodetector 107 is that reflected right off the skin surface 1003.

In the illustrated embodiment, the light-blocking screen 110 is driven by a mechanical oscillator 30 so that transmissive and reflective light measurements be performed alternately.

The temperature of the transducer is thermostatically controlled by a system here shown only to the extent of its heating coil 12 and its temperature sensor 11.

As explained initially, the light signal produced by photodetector 106 can be used to determine, by means of photoelectric plethysmography, the volumetric rate of flow of blood through the skin's capillary network. At the same time, in accordance with the conventional Hensel method, the amount of heat energy which the thermostatic system of the transducer consumes to maintain constant temperature can be used to determine the total volumetric rate of flow of blood through the tissue of interest, accordingly making it possible with the novel transducer to ascertain the volumetric rate of blood flow in the tissue exclusive of blood flow through its capillary network.

Advantageously, for both reflective and transmissive measurements, wavelenghts of about 1.2 microns are employed, because at such wavelengths hemoglobin reaches an invariant point and the factor of skin pigmentation no longer plays any considerable role.

The multi-purpose blood-gas concentration transducer of the present invention serves to greatly open up the utility and variety of measurements which can be performed.

It will be understood that each of the elements described above, or two or more together, may also find a useful application in other types of constructions differing from the types described above.

While the invention has been illustrated and described as embodied in a multi-purpose blood-gas concentration transducer adapted for polarographic oxygen-concentration measurement, it is not intended to be limited to the details shown, since various modifications and structural changes may be made without departing in any way from the spirit of the present invention.

Without further analysis, the foregoing will so fully reveal the gist of the present invention that others can, by applying current knowledge, readily adapt it for various applications without omitting features that, from the standpoint of prior art, fairly constitute essential characteristics of the generic or specific aspects of this invention.

What is claimed as new and desired to be protected by Letters Patent is set forth in the appended claims.

1. An improved blood-gas concentration transducer of the type employed for the transcutaneous measurement of blood-gas concentration and blood flow rate and comprised of reference and measuring electrodes and having a face which is laid against the tissue of interest for transcutaneous measurement, the improvement comprising light-emitting means operative for emitting light from said face for incidence onto the tissue against which said face of the transducer is laid, and photodetector means operative for receiving light transmitted in the direction towards said face of the transducer from the tissue against which said face is laid.

2. The transducer defined in claim 1, the light source comprising a light-emitting diode.

3. The transducer defined in claim 1, the light-emitting means comprising a light-emitting element and a light-conductive element transmitting light from the light-emitting element to the tissue against which said face of the transducer is laid.

4. The transducer defined in claim 1, the transducer including a structure having a light-guiding bore serving to guide light from the light-emitting means to the tissue against which said face of the transducer is laid.

5. The transducer defined in claim 1, the light-emitting means and the photodetector means comprising a plurality of monochromatic light sources and a plurality of photodetectors.

6. The transducer defined in claim 1, the photodetector means including a light-conductive element located to conduct light away from the tissue.

7. The transducer defined in claim 1, the transducer including a structure having a light-guiding bore oriented to guide light transmitted from the tissue against which said face of the transducer is laid.

8. The transducer defined in claim 1, the light-emitting means comprising means for emitting light onto the tissue against which said face of the transducer is laid at an angle to the normal to said face, the photodetector means comprising means operative for receiving light transmitted from the tissue at an angle to the normal to said face.

9. The transducer defined in claim 8, the light received by the photodetector means being light received from the selfsame part of the tissue onto which the light emitted onto the tissue is incident.

10. The transducer defined in claim 9, furthermore including a light-blocking screen mounted in the transducer in a position to prevent the light emitted onto the tissue from being directly reflected to the photodetector means but instead constraining the light emitted onto the tissue to pass through the tissue and emerge therefrom and only then be received by the photodetector means, the screen being removable from said position.

11. The transducer defined in claim 10, the light-blocking screen being displaceably mounted in the transducer between said position and a non-blocking position removed therefrom.

12. The transducer defined in claim 11, furthermore including drive means for automatically moving the light-blocking screen between the two positions thereof.

* * * * *